(12) United States Patent
Kargar et al.

(10) Patent No.: US 7,693,909 B2
(45) Date of Patent: Apr. 6, 2010

(54) METHOD FOR INTEGRATING QUANTITATIVE MEASUREMENTS OF IMAGING SYSTEMS WITH REPORTING APPLICATIONS OF MEDICAL RECORDING SYSTEMS

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 337 days.

(21) Appl. No.: 11/832,126

(22) Filed: Aug. 1, 2007

(65) Prior Publication Data

US 2008/0270423 A1    Oct. 30, 2008

Related U.S. Application Data

(60) Provisional application No. 60/913,910, filed on Apr. 25, 2007.

(51) Int. Cl.
*G06F 17/60* (2006.01)

(52) U.S. Cl. ............... 707/758; 707/915; 707/E17.012; 705/2; 709/203; 709/219

(58) Field of Classification Search .......... 707/E17.012, 707/999.01, 999.1, 999.101, 999.107; 705/2; 709/203, 219
See application file for complete search history.

(56) References Cited

U.S. PATENT DOCUMENTS

| | | | | |
|---|---|---|---|---|
| 5,872,861 | A | * | 2/1999 | Makram-Ebeid ............ 382/130 |
| 6,090,047 | A | * | 7/2000 | Kass et al. .................. 600/485 |
| 7,233,329 | B2 | | 6/2007 | Moreau-Gobard |
| 2002/0035566 | A1 | * | 3/2002 | Rugg et al. ................. 707/100 |

OTHER PUBLICATIONS

Cornell University, "Table: Common Image File Formats", 2000-2002, Cornell University Library/Research Department, http://www.library.cornell.edu/preservation/tutorial/presentation/table7-1.html, pp. 2.*

* cited by examiner

*Primary Examiner*—Mohammad Ali
*Assistant Examiner*—Amanda Willis
(74) *Attorney, Agent, or Firm*—Alexander J Burke

(57) ABSTRACT

A method and system for reporting quantitative measurement information includes forming a message with quantitative measurement information; converting the data format of the message to a data format which allows the message to be sent over a communication network; converting the data format of the message received over the communication network to a data format corresponding to that of a data recording system; and generating a report with the recording system using the quantitative measurement information contained in the message.

19 Claims, 3 Drawing Sheets

US 7,693,909 B2

METHOD FOR INTEGRATING QUANTITATIVE MEASUREMENTS OF IMAGING SYSTEMS WITH REPORTING APPLICATIONS OF MEDICAL RECORDING SYSTEMS

RELATED APPLICATIONS

This application claims the benefit of U.S. Provisional Application Ser. No. 60/913,910 filed on Apr. 25, 2007, the entire disclosure of which is incorporated herein by reference.

FIELD

Embodiments of the present invention relates to data processing. More particularly, embodiments of the present invention relates to automating the reporting workflow associated with a quantitative analysis application running on an imaging system and a reporting application running on a recording system.

BACKGROUND

Software applications that combine angiography and computer image enhancement are commonly referred to as quantitative cardiac image analysis (QCIA). The QCIA application provides calibration capability, such as sphere, distance, catheter, and manual calibrations, and offers quantitative coronary analysis (QCA), quantitative vascular analysis (QVA), and left ventricle analysis (LVA).

Cardiologists and radiologists use QCIA software applications to generate data about the human vascular system. This data helps the doctor diagnose vascular diseases and determine appropriate treatment strategies.

The QCA application processes angiographic images of the coronary arteries to determine the diametrical dimensions of the coronary arteries. Accordingly, QCA may be used for measuring narrowing (stenosis) of the coronary arteries.

The QVA application processes angiographic images of the other blood vessels of the body to determine diametrical dimensions of these blood vessels. Accordingly, QVA may be used for measuring stenoses in other blood vessels.

Artery contour detection can be performed (for QCA and QVA) by defining the vascular segment of interest and marking an approximate center line of the segment in the direction of blood flow.

The LVA application processes angiographic images of the heart to quantitatively analyze left ventricular function using images in one or two acquisition planes to capture the left ventricle in different angulations, such as a 30° right anterior oblique (RAO) view and a 60° left anterior oblique (LAO) view. This allows the blood volume of the left ventricle, ejection fraction, etc, to be determined.

A coronary tree illustrator (CTI) is a software application that may be used to report the results of a cardiac catheterization study (cath reporting). This application allows the doctor to illustrate coronary dominance, collaterals, grafts, stenoses and interventions with corresponding characteristics. A number of pre-defined sites named and located according to the AHA conventions can be used for definition of coronary anomalies.

After performing QCA and deciding the best suited therapy for the patient, the doctor documents the diagnosis and the treatment that has been performed. As part of cath reporting, the doctor must document the quantitative measurements that were performed with the QCA application in the CTI application. This is currently performed by manually copying or inputting the quantitative measurements (e.g., stenotic length, etc.) into the CTI application, thus populating the CTI application with pre and post cath findings which are used to create a cath report.

Accordingly, a method is needed which eliminates the need to manually copy or input the quantitative measurements obtained via the QCA application to the CTI application.

SUMMARY

Disclosed herein is a method for reporting quantitative measurement information. The method comprises the steps of forming a message comprising quantitative measurement information generated by an imaging system, the message formed in a first data format corresponding to that of the imaging system; converting the first data format of the message to a second data format which allows the message to be sent over a communication network; sending the message over the communication network to a data recording system using the second data format; converting the second data format of the message received over the communication network by the data recording system to a third data format corresponding to that of the data recording system; and generating a report with the data recording system using the quantitative measurement information contained in the message.

Also disclosed herein is a system for obtaining and reporting quantitative measurement information. The system comprises an imaging system including an imaging device for obtaining an image, a first computer running a quantitative analysis application that quantitatively analyzes the image and forms a message comprising quantitative measurement information in a first data format corresponding to that of the imaging system, and a first converter for converting the first data format of the message to a second data format which allows the message to be sent over a communication network; and a data recording system connected via the communication network to the imaging system so that the data recording system can receive the message when sent by the imaging system over the communication network, the data recording system including a second computer running a data reporting application for generating a report using the quantitative measurement information contained in the message and a second converter for converting the second data format of the message to a third data format corresponding to that of the data recording system so that the data reporting application can use the quantitative measurement information contained therein to generate the report.

DETAILED DESCRIPTION

The present disclosure is directed to automating the reporting workflow associated with a quantitative analysis application (quant application) running on an imaging system and a reporting application running on a recording system. In accordance with the principles of the invention, the analytical data (quantitative measurements) generated by the quant application is automatically inputted into the reporting application.

Figure 1:
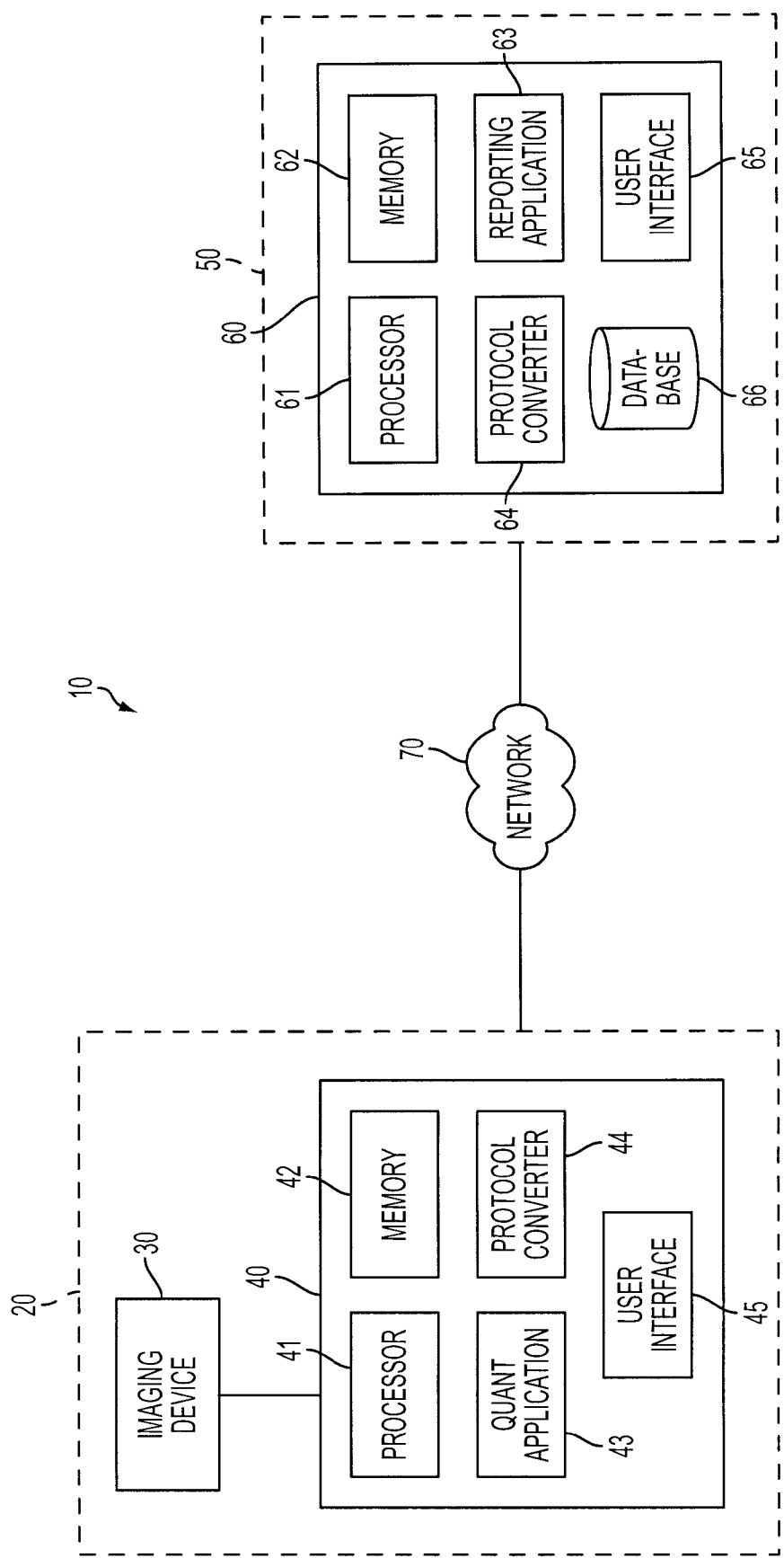
FIG. 1 is a block diagram of an exemplary embodiment of a system according to the present disclosure.

FIG. 1 is block diagram of an exemplary embodiment of a system according to the present disclosure. The system 10 comprises an imaging system 20 communicatively connected to a recording system 50 via a communication network 70 including, but not limited to the internet.

The imaging system 20 includes an imaging device 30 that acquires medical images. The imaging device 30 may be an x-ray imaging device that performs digital radiography, a DSA imaging device that performs digital subtraction angiography, an MR imaging device that performs magnetic resonance imaging, or a CT imaging device for performing computed tomography, to name a few.

The imaging system also includes a first computer 40 with a processor 41, a memory 42, and a user interface 45. The user interface 45 may include suitable input devices including, without limitation, a keypad and a mouse, and suitable output devices including, without limitation, a display screen and a printer. The first computer 40 may also include other known computer components for enabling operation thereof in the imaging system 20.

The first computer 40 further includes an application 43 for performing quantitative analysis on selected images acquired by the imaging device 30 and a first communication protocol converter 44 for converting or changing the data format or communication protocol of quantitatively analyzed image data generated by the quant application 43 (quant data) when this data is sent by the imaging system 20 in a message over the communication network 70 to the recording system 50. More specifically, when the imaging system 20 creates the message comprising the quant data generated by the quant application, the data is formatted in the data format or communication protocol of the imaging system 20. The first converter 44 may be implemented in software, hardware, or a combination of both, and converts or changes the data format of the message to a data format or communication protocol that allows the message to be transmitted or sent over the communication network without changing the content (quant data) of the message. Because methods for converting from one data format to another are well known in the art no further discussion is needed herein.

The recording system 50 includes a second computer 60 with a processor 61, a memory 62, and a user interface 65. The user interface 65 may include suitable input devices including, without limitation, a keypad and a mouse, and suitable output devices including, without limitation, a display screen and a printer. The second computer 60 may also include other known computer components for enabling operation of the computer in the recording system 50.

The second computer 60 further includes a reporting application 63 for generating a report using the quant data contained in the message received from the imaging system 20 over the communication network 70, a database 66 for storing the quant data so that the report can be generated at a later time or so additional reports can be generated at later times. Also included is a second communication protocol converter 64 for converting or changing the data format or communication protocol of the message received from the communication network 70 to the data format or communication protocol of the recording system 50, which may be different from or the same as the data format or communication protocol of the imaging system 20. In either case, the data format must be changed to that of the recording system 50. The second converter 64 performs this function, thereby enabling the recording system 50 to read the quant data contained in the message. The second converter 64 may also be implemented in software, hardware, or a combination of both.

The recording system saves the quant data for each study in the database. When a user retrieves a report for a selected study, the reporting application automatically populates a report template with all the quant data for the selected study saved in the database. This will help to improve reporting turnaround time and eliminates possible data entry mistakes.

In a preferred embodiment, the imaging system is an x-ray imaging system, the quant application is QCIA (quantitative cardiac imaging analysis) application, the recording system is a hemodynamics recording system, the reporting application is a CTI application, and the report is a cath report. The quant data generated by the QCIA application relates to coronary stenosis including, without limitation, size of the stenosis, anatomical position of the stenosis, percentage of the stenosis and eccentricity of the stenosis, generated by the QCIA application running on the x-ray system is automatically inputted into the CIT application of the hemodynamics recording system.

Figure 2:
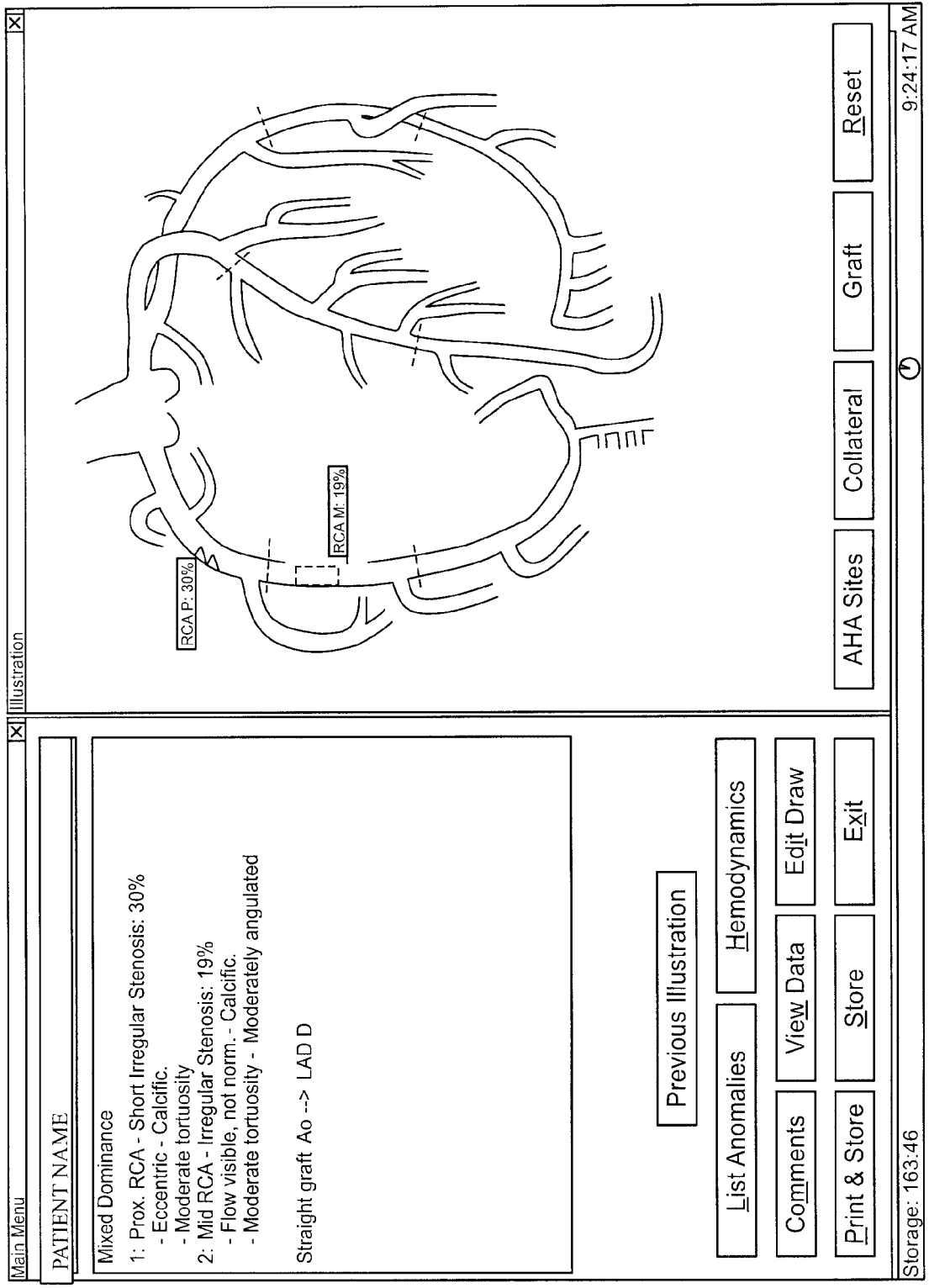
FIG. 2 is an exemplary embodiment of a report generated by the reporting application of the recording system.

FIG. 2 is an exemplary embodiment of a report generated by the reporting application of the recording system. As can be seen, the quant data can be textually and/or graphically displayed or printed in a report.

The integration of the quant and reporting applications of the imaging and recording systems, respectively, eliminates the need for the user (e.g., cardiologists and other doctors) to manually input diagnostic, therapeutic result, and other information and data generated by the quant application into the reporting application. Accordingly, user reporting efficiency is improved and the possibility of mistakes caused by manual data entry from the quant application to the reporting application is reduced.

Figure 3:
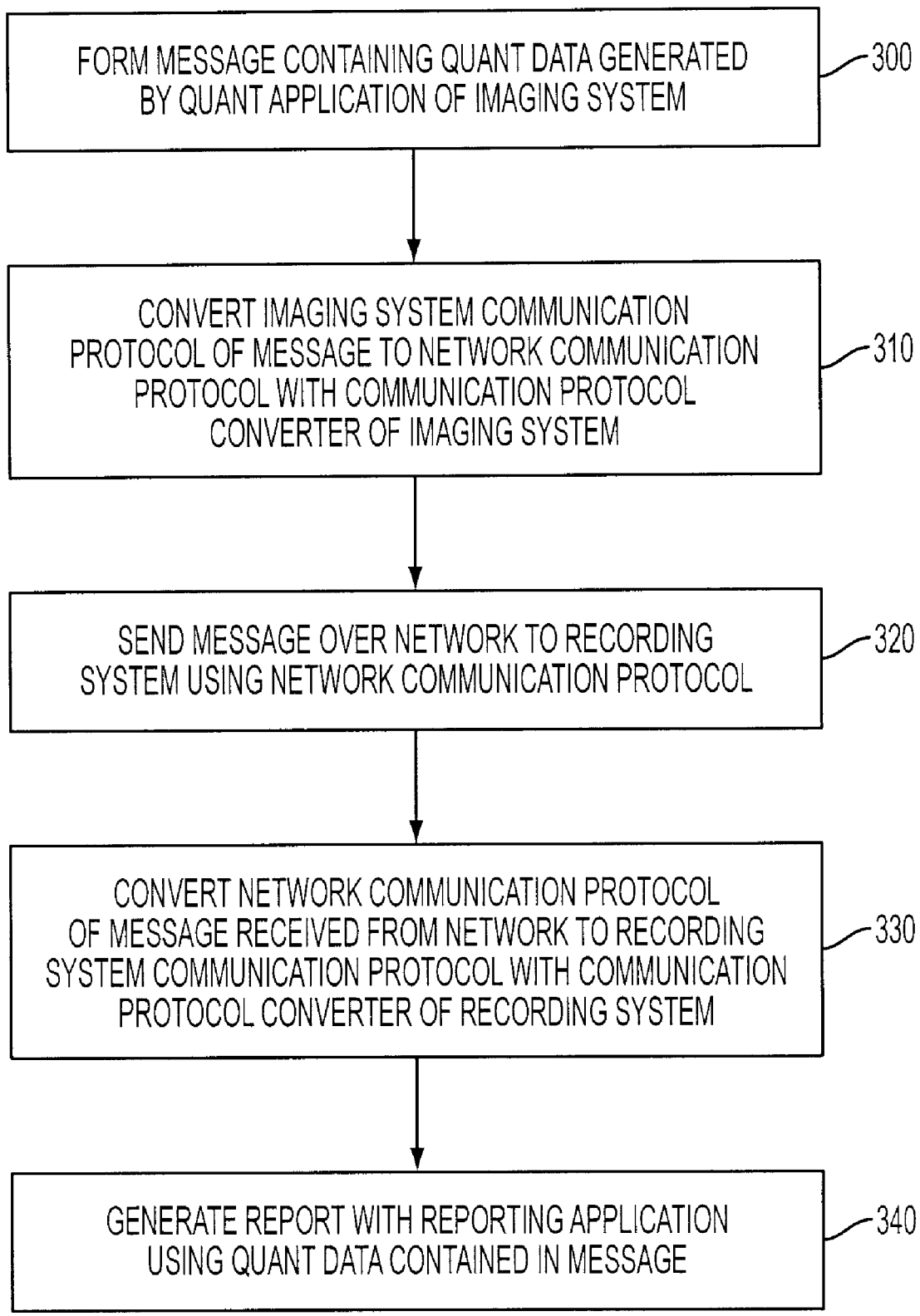
FIG. 3 is a flow chart of an exemplary embodiment of a method for automating the reporting workflow associated with a quant application and a reporting application according to the present disclosure.

FIG. 3 is flow chart of an exemplary embodiment of a method for automating the reporting workflow associated with a quant application and a reporting application according to the present disclosure. For illustrative purposes only, the method will be described in the context of a cardiology reporting workflow and the system shown in FIG. 1. Persons of ordinary skill in the art will of course appreciate that the method described herein can be applied to other medical and non-medical workflows and other systems.

Preliminary to the method, an image of the heart is selected and displayed on a display screen of the imaging system 20 (FIG. 1). In the context of the cardiology workflow, the imaging system typically comprises an x-ray imaging system and the image therefore comprises an x-ray image of the heart. The user then launches a quantitative analysis application to quantitatively analyze the x-ray image of the heart. In one embodiment, the quant application is a quantitative coronary analysis (QCA) application. The user operates QCA application to perform a quantitative analysis of the coronary arteries (QCA) of the heart shown in the x-ray image. In one exemplary embodiment, the user may perform the quant analysis by drawing an approximate center line in a vascular segment of the heart shown in the x-ray image that requires examination.

Referring now to the method depicted in the flowchart of FIG. 3, the quant application forms a message containing quantitative measurements (e.g., angulations, stenotic length and other results) of the vascular segment in step 300. The message is formed in the data format or communication protocol of the x-ray imaging system.

In step 310, the first communication protocol converter 44 of the x-ray imaging system converts the data format of the message to the data format or communication protocol of the communication network 70.

In step 320, the message is sent over the network 70 using the data format or communication protocol of the communication network 70 and received by the recording system 50.

In step 330, the second communication protocol converter 64 of the recording system converts the data format of the message to the data format or communication protocol of the recording system 50. The quant data may be saved in the database 66 as an identifiable cardio study file for use later on.

In step 340, the user selects the desired cardio study file saved in the database 66 for reporting and the CTI application 63 automatically populates a cath report template with all the quant data from the selected cardio study file saved in the database 66 and displays or prints this as a cath report. Based on the C-arm angles of the selected x-ray image that the quant was being performed on, the left or right coronary artery will be differentiated. The CTI application will select the correct vessel for processing and the size and anatomical position of the stenosis will be passed to the CTI application and displayed in picture of the heart in the cath report.

The present disclosure reduces the time needed for the creating the cath report and virtually eliminates the possibility of mistakes during the manual data entry. By opening the CTI application, all the quantitative measurements are displayed and the user merely needs to check the report for possible addition of other diagnostic information if required. The manual process of drawing the stenosis and inputting other information is eliminated with the present disclosure.

Embodiments of the present invention may be embodied in other specific forms without departing from the spirit or essential attributes of the disclosure. Accordingly, reference should be made to the appended claims, rather than the foregoing specification, as indicating the scope of embodiments of the invention. Although the foregoing description is directed to exemplary embodiments, it is noted that other variations and modification will be apparent to those skilled in the art, and may be made without departing from the spirit or scope of the invention.

What is claimed is:

1. A computer implemented method for reporting quantitative measurement information including stenosis related information, the method comprising the steps of:
    forming a message comprising vascular quantitative measurement information generated by a quantitative measurement application executing on an imaging system, the message including vascular morphology information comprising stenosis information and being in a first data format corresponding to that of the imaging system;
    sending the formed message over a communication network to a data recording system including a coronary tree application;
    using the coronary tree application for presenting the vascular morphology information in a pictorial representation of coronary vasculature and said coronary tree application selects a vessel for processing and the size and anatomical position of stenosis is passed to the coronary tree application and displayed in a picture of the heart in a catheterization report; and
    employing the coronary tree application in generating a report including the vascular morphology information derived using the quantitative measurement application and contained in the message.

2. The method of claim 1, including a quantitative analysis application that generates the quantitative measurement information and the coronary tree application uses X-ray system C-arm angle data of an X-ray image on which quantitative measurement is being performed to identify a left or right coronary artery as being associated with said vascular morphology information and presents said vascular morphology information in a pictorial representation of the identified left or right coronary artery in said coronary vasculature.

3. The method of claim 2, wherein the quantitative analysis application performs at least one of quantitative coronary analysis, quantitative vascular analysis, and left ventricle analysis and the vascular morphology information includes left ventricle volume information.

4. The method of claim 1, wherein the imaging system comprises an x-ray imaging system and the coronary tree application automatically populates a catheterization report template with quantification data including the vascular morphology information and the pictorial representation of coronary vasculature.

5. The method of claim 1, including the steps of
    converting the first data format of the message to a second data format which allows the message to be sent over a communication network and
    converting the second data format of the message received over the communication network to a third data format.

6. The method of claim 1, wherein the the coronary tree application automatically populates a catheterization report template with quantification data from a selected cardiac image study file in a database and displays the report as a catheterization report.

7. The method of claim 1, wherein the coronary tree application selects a left or right vessel for Processing based on C-arm angle data and the size and anatomical position of stenosis is passed to the coronary tree application and displayed in a picture of the heart in a catheterization report.

8. The method of claim 5, wherein the first and third data formats are identical.

9. The method of claim 5, wherein the first and third data formats are different.

10. The method of claim 1, wherein the quantitative measurement information includes analytical coronary artery imaging data, the report providing at least one of an illustration and description of the analytical coronary artery imaging data.

11. The method of claim 1, further comprising the step of saving the analytical data to a database prior to the report generating step, wherein the report generating step uses the quantitative measurement information saved in the database.

12. A system for obtaining and reporting quantitative measurement information including stenosis related information, the system comprising:
    an imaging system including,
        an imaging device for obtaining an image,
        a first computer executing a quantitative analysis application that quantitatively analyzes the image and forms a message comprising quantitative measurement information including vascular morphology information comprising stenosis information and being in a first data format corresponding to that of the imaging system; and
    a data recording system connected a communication network to the imaging system so that the data recording system can receive the message when sent by the imaging system over the communication network, the data recording system including,
        a second computer executing a data reporting application comprising a coronary tree application for generating a report using the quantitative measurement information including the vascular morphology information derived using the quantitative analysis application contained in the message and presenting the vascular morphology information in a pictorial representation of coronary vasculature and said coronary tree application selects a vessel for processing in response to X-ray system angle data.

13. The system of claim 12, wherein the quantitative analysis application performs at least one of quantitative coronary analysis, quantitative vascular analysis, and left ventricle analysis and said coronary tree application selects a vessel for processing based on C-arm angle data and the size and anatomical position of stenosis is passed to the coronary tree application and displayed in a picture of the heart in a catheterization report.

14. The system of claim 12, wherein the imaging system comprises an x-ray imaging system and the coronary tree application automatically populates a catheterization report template with quantification data including the vascular morphology information and the pictorial representation of coronary vasculature.

15. The system of claim 12, wherein
said imaging system converts the first data format of the message to a second data format which allows the message to be sent over the communication network and said data recording system converts the second data format of the message received over the communication network to a third data format.

16. The system of claim 12, wherein the coronary tree application selects a correct vessel for processing and the size and anatomical position of stenosis is passed to the coronary tree application and displayed in a picture of the heart in a catheterization report.

17. The system of claim 15, wherein the first and third data formats are identical.

18. The system of claim 15, wherein the first and third data formats are different.

19. The system of claim 12, wherein the quantitative measurement information includes analytical coronary artery imaging data, the report providing at least one of an illustration and description of the analytical coronary artery imaging data.

* * * * *